US008045740B2

(12) United States Patent
Klemenz et al.

(10) Patent No.: US 8,045,740 B2
(45) Date of Patent: Oct. 25, 2011

(54) IN-THE-EAR HEARING APPARATUS HAVING A BAND ELEMENT FOR ATTACHING A HOUSING PART

(75) Inventors: Harald Klemenz, Fürth (DE); Tom Weidner, Erlangen (DE)

(73) Assignee: Siemens Audiologische Technik GmbH, Erlangen (DE)

( * ) Notice: Subject to any disclaimer, the term of this patent is extended or adjusted under 35 U.S.C. 154(b) by 1254 days.

(21) Appl. No.: 11/725,420

(22) Filed: Mar. 19, 2007

(65) Prior Publication Data

US 2007/0230730 A1 Oct. 4, 2007

(30) Foreign Application Priority Data

Mar. 30, 2006 (DE) ......................... 10 2006 014 884

(51) Int. Cl.
*H04R 25/00* (2006.01)
*A61N 1/00* (2006.01)

(52) U.S. Cl. ........... 381/324; 381/322; 206/805; 607/56

(58) Field of Classification Search .................. 381/312, 381/322, 324; 607/56–57; 600/25; 206/805; 49/173

See application file for complete search history.

(56) References Cited

U.S. PATENT DOCUMENTS

| | | | | |
|---|---|---|---|---|
| 2,659,772 | A | 11/1953 | O'Hara | |
| 3,688,435 | A | 9/1972 | Sapkus et al. | |
| 4,702,345 | A * | 10/1987 | Janssen et al. | 181/129 |
| 5,530,763 | A | 6/1996 | Aebi et al. | |
| 6,144,749 | A * | 11/2000 | Fideler | 381/323 |
| 6,473,512 | B1 | 10/2002 | Juneau et al. | |
| 6,728,383 | B1 * | 4/2004 | Juneau et al. | 381/322 |
| 2005/0117765 | A1 * | 6/2005 | Meyer et al. | 381/322 |
| 2007/0036379 | A1 * | 2/2007 | Anderson et al. | 381/324 |

FOREIGN PATENT DOCUMENTS

EP 0629 101 A1 12/1994

* cited by examiner

*Primary Examiner* — Curtis Kuntz
*Assistant Examiner* — Jesse Elbin

(57) ABSTRACT

A hearing device opening in a housing of an in-the-ear hearing device is to be able to be sealed in a simple manner. To this end, an elastic band is provided, which is attached to a second housing part and/or faceplate and to a first housing part or inside the second housing part. The band pulls the second housing part into the corresponding opening of the first housing part. The second housing part is herewith automatically brought into position and retained. An electrical component can be mounted on the elastic band if necessary.

17 Claims, 2 Drawing Sheets

IN-THE-EAR HEARING APPARATUS HAVING A BAND ELEMENT FOR ATTACHING A HOUSING PART

CROSS REFERENCE TO RELATED APPLICATIONS

This application claims priority of German application No. 10 2006 014 884.3 filed Mar. 30, 2006, which is incorporated by reference herein in its entirety.

FIELD OF THE INVENTION

The present invention relates to an in-the-ear hearing apparatus having a first housing part and a second housing part, with which the first housing part can be sealed. In particular, the invention relates to in-the-ear hearing devices. Nevertheless, other hearing apparatuses, such as pure receivers of headsets, which can be inserted into the auditory canal, can profit from the invention.

BACKGROUND OF THE INVENTION

In-the-ear hearing devices typically possess an individually tailored hearing device shell. This is usually sealed from the outside environment by a so-called faceplate or another housing part. If the faceplace or housing part is removed from the hearing device shell, the battery of the hearing device or however also other electronics components are generally accessible. In many cases, the faceplate and/or housing part is designed as one-piece with a battery compartment, so that the battery is pivoted outwards when the faceplate is opened. A faceplate and/or housing part of this type thus allows a (semi-) modular design of the in-the-ear hearing device.

The faceplate is mostly mounted or otherwise attached to the shell, i.e. the hearing device housing. It has hitherto been attached for instance by means of locking mechanisms or screw connections.

Even if the faceplate can be opened in the case of modular hearing devices, or can be removed from the shell, an adequate impermeability of the hearing device must be guaranteed. Consequently, very precise manufacturing methods for producing the hearing device shell and the faceplate are necessary. In addition, a mechanical seal having small complex structures is necessary, which can only be manufactured with extreme difficulty. Known SLA/SLS methods are currently used for this purpose. In addition, the seal requires some installation space, which in itself is a precious resource in-the-ear hearing devices.

The publication U.S. Pat. No. 6,473,512 B1 discloses a hearing aid, in which a cantilever connects a disk with a support, which is located on the eardrum side end of the hearing aid. The cantilever serves to provide stability in the longitudinal direction and reduces both extension and also compression.

Furthermore, the publication EP 0 629 101 A1 discloses a hearing aid to be worn in the ear having a skeleton, with which the skeleton is composed of an external faceplate, an inner faceplate and a connecting element. The connecting element can be deformed to a limited degree and is intended to maintain the position of the two faceplates, while the intermediate space is sealed.

SUMMARY OF THE INVENTION

The object of the present invention thus consists in proposing an in-the-ear hearing apparatus, the first housing part of which can be sufficiently compactly sealed, with the second housing part being attached to the first housing part in a simple manner and without wasting installation space.

In accordance with the invention, this object is achieved by an in-the-ear hearing apparatus having a first housing part and a second housing part or a module, with which the first housing part can be sealed, as well as a flexible elastic element which can be extended in the longitudinal direction, said elastic element being attached on the one hand to the first housing part or to the inside of the first housing part and on the other hand to the second housing part and/or to the module or a part thereof, and which is pretensioned to pull the second housing part and/or the module onto the first housing part.

A rubber band can advantageously be used as a flexible elastic element for instance, so that less space is required for the sealing mechanism and the hearing device can additionally be assembled with fewer components. Furthermore, the module and/or the second housing part or the faceplate, which is supported by the elastic element exclusively by means of tension, can be easily removed from the first housing part and as a result of the tension, no gaps appear between the first and the second housing part. Furthermore, fewer precision requirements are set on the manufacturing process for the hearing device shell, i.e. the first housing part, as well as the faceplate, i.e. the second housing part, and the module, since the elastic element pulls the second housing part and/or the module automatically into a predetermined closed position, particularly if the edges are designed to be correspondingly wedge-shaped. A further advantage of the solution according to the invention thus consists in the fact that the hearing device generally becomes more mechanically stable as a result of the elastic element attachment.

The elastic element is preferably provided with one or more additional arms and thus is star-shaped and possesses at least three elastic ends. In this case, the individual arms of the elastic element can be extended in each instance in the longitudinal direction. The free elastic ends can be attached to the first or the second housing part or the module depending on requirements. The star shape allows the second housing part and/or the module to be better moved into the desired spatial position. It can be favorable for instance for two of the elastic ends are attached to the second housing part and a third elastic end is attached to the first housing part. In another case, it can be advantageous if two of the elastic ends are attached to the first housing part and only one thereof is attached to the second housing part. If more than three arms of the elastic element and/or elastic ends are provided, these can be distributed in any manner on the second housing part and/or module and the first housing part.

A particularly preferred further development of the invention consists of an electronic component of the hearing apparatus being attached to the elastic element. This electronic component can be attached in the center of the star-shaped elastic element for instance. A coil or a loudspeaker or receiver could be considered here as an electronic component for instance. The support on the elastic element is advantageous in that no other fixing options need to be provided. Furthermore, the support with the flexible elastic element is advantageous for the receiver and/or loudspeaker for instance in that feedbacks over the housing are avoided and/or reduced.

Furthermore, an elastic segment of the elastic element can be designed in the shape of a tube, and can conduct the sound from the output of the loudspeaker out of the housing. In this way, the additional functionality of a sound tube is produced for the elastic element. This tubular elastic segment can simultaneously serve to apply the desired force to support the second housing part and/or the module, by correspondingly fixing it in or to the first housing part.

The elastic element can furthermore be attached to the housing segment, which faces the eardrum when being worn in the ear and does not rest against the auditory canal. This is advantageous in that the elastic element can then be affixed to the exterior of the hearing device housing, without any complex fixing mechanism, without disturbing the auditory canal.

BRIEF DESCRIPTION OF THE DRAWINGS

The present invention is now described in more detail with reference to the appended drawings, in which.

DETAILED DESCRIPTION OF THE INVENTION

The exemplary embodiments illustrated in more detail below represent preferred embodiments of the present invention.

Figure 1:
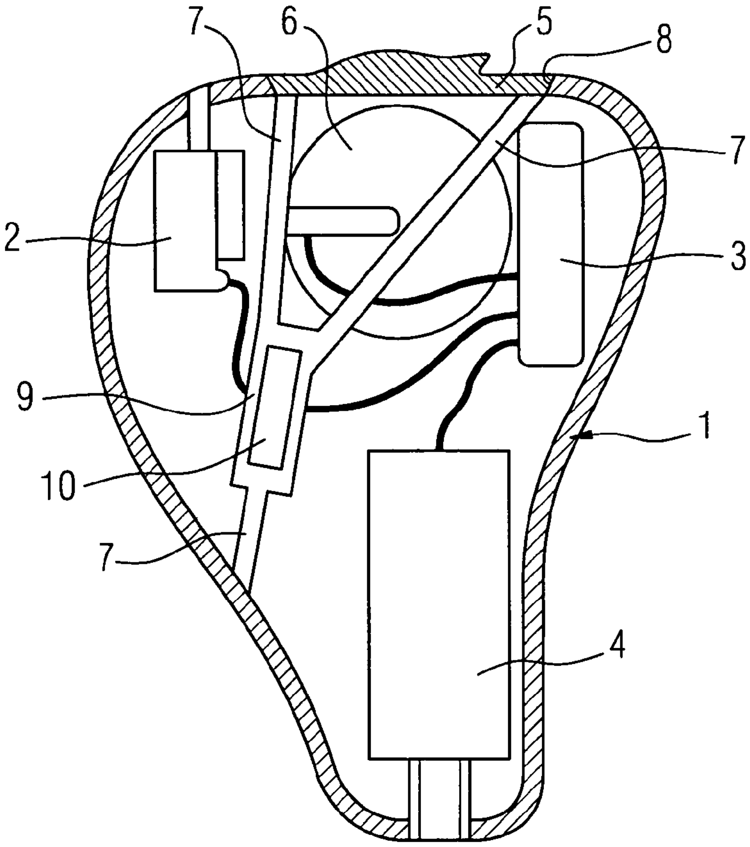
FIG. 1 shows a first embodiment of the present invention with a rubber band-supported coil.

FIG. 1 shows a cross-sectional view of an in-the-ear hearing device according to a first embodiment of the present invention. It features a hearing device housing and/or a shell, in which a microphone 2, a hybrid circuit 3 and a receiver are accommodated. The shell 1 (first housing part) is sealed with a faceplate 5 (second housing part), which is equipped with a battery compartment for accommodating a battery 6.

The faceplate 5, including the battery compartment, is retained in an opening 8 of the hearing device shell 1 with the aid of a rubber band 7. The rubber band 7 is designed here with three arms, which feature a common star point 9. Two of the armbands are attached to the faceplate 5 and a further band end is affixed to the housing 1. The attachment to the housing is carried out by means of adhesion for instance.

In the center 9, the rubber band 7 is equipped with a support, which supports a coil 10 in the present example. A corresponding dimensioning of the rubber band 7, i.e. the elastic element, as well as a suitable selection of the attachment points of the elastic end allow the coil 10 to be mounted in a defined position compared with the receiver 4 for instance, so that magnetic parasitic inductions are avoided as far as possible. The rubber band 7 allows the faceplate 5 to be automatically attached and retained in the desired position. Furthermore, the faceplate 5 can be easily removed again, since it is exclusively held by means of tension.

As the rubber band 7, which holds the faceplate 5 on the shell 1, is used simultaneously as a support for the coil or another component, a fixed support option in the hearing device can be dispensed with and the other internal components can be positioned more easily under some circumstances.

Figure 2:
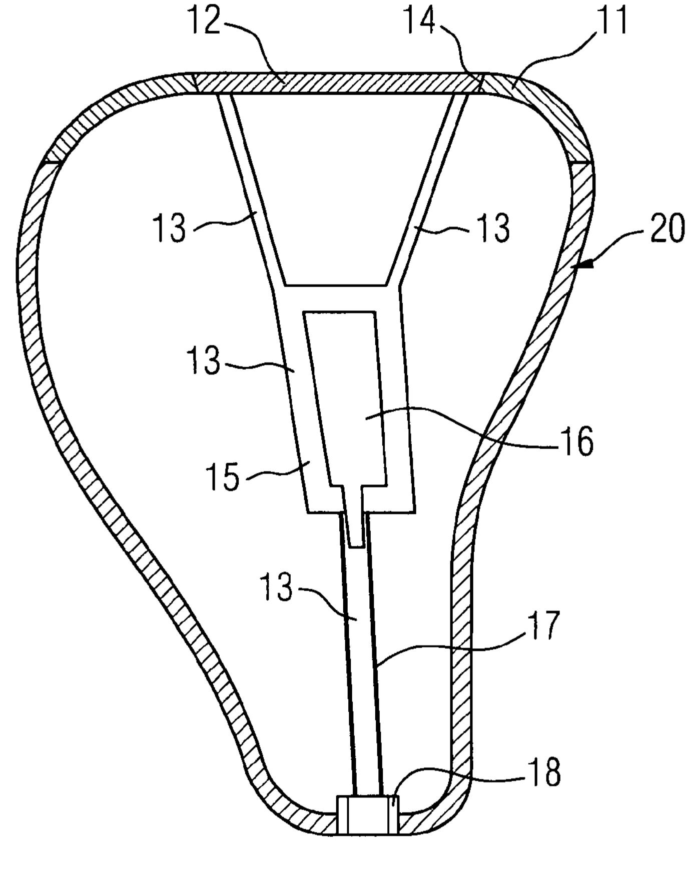
FIG. 2 shows a second embodiment of the present invention with a rubber band-support receiver and faceplate and FIG. 3 shows third embodiment of the present invention having two housing parts.

FIG. 2 shows a cross-sectional illustration of an in-the-ear hearing device according to a second embodiment of the present invention. To provide a better overview a circuit module, a microphone, a battery and a coil are not shown in the diagram. The hearing device shell 20 is sealed from the outside environment by a faceplate 11 (when positioned in the ear). The faceplate 11 can also be designed in one piece with the hearing device shell 20. This faceplate 11 comprises a removable segment 12, to which a battery compartment or another electronics component can be attached for instance, so that the element 12 can also be referred to as a module. An elastic band 13 pulls the module 12 into the faceplate 11. This elastic band 13 is attached to the module 12 with two arms, corresponding to the example illustrated, and with a third arm on the side of the hearing device shell 20 facing the ear drum. As the faceplate 11 has a conical opening 14, and the module 12 is profiled accordingly, it is automatically pulled into the correct position by means of the elastic band 13.

In the center, the rubber band 13 is provided with a recess 15, as also in the first exemplary embodiment, into which recess a receiver 16 is inserted. The arm of the elastic band from the receiver 16 to the segment of the hearing device shell facing the ear drum is designed as a receiver tube 17, in order to direct the sound from the receiver to the end of the housing. The tube 17 is additionally affixed to a support of the receiver 16. The receiver 16 is thus mounted fully elastically in the hearing device shell 20, so that there is no danger of feedbacks over the hearing device shell 20.

To install the rubber band 13, the receiver tube 17 is inserted into the shell 20 through a receiver-side opening. It is held there by means of a sealing mechanism 18. This sealing mechanism can be realized by means of adhesion, clamping, screwing etc. In any event, the module 12 is pulled into the opening 14 of the faceplate by virtue of the elasticity of the rubber band 13 after the receiver tube 17 is attached. Alternatively, the receiver tube 17 can also be screwed together with a cerumen protection device.

Figure 3:
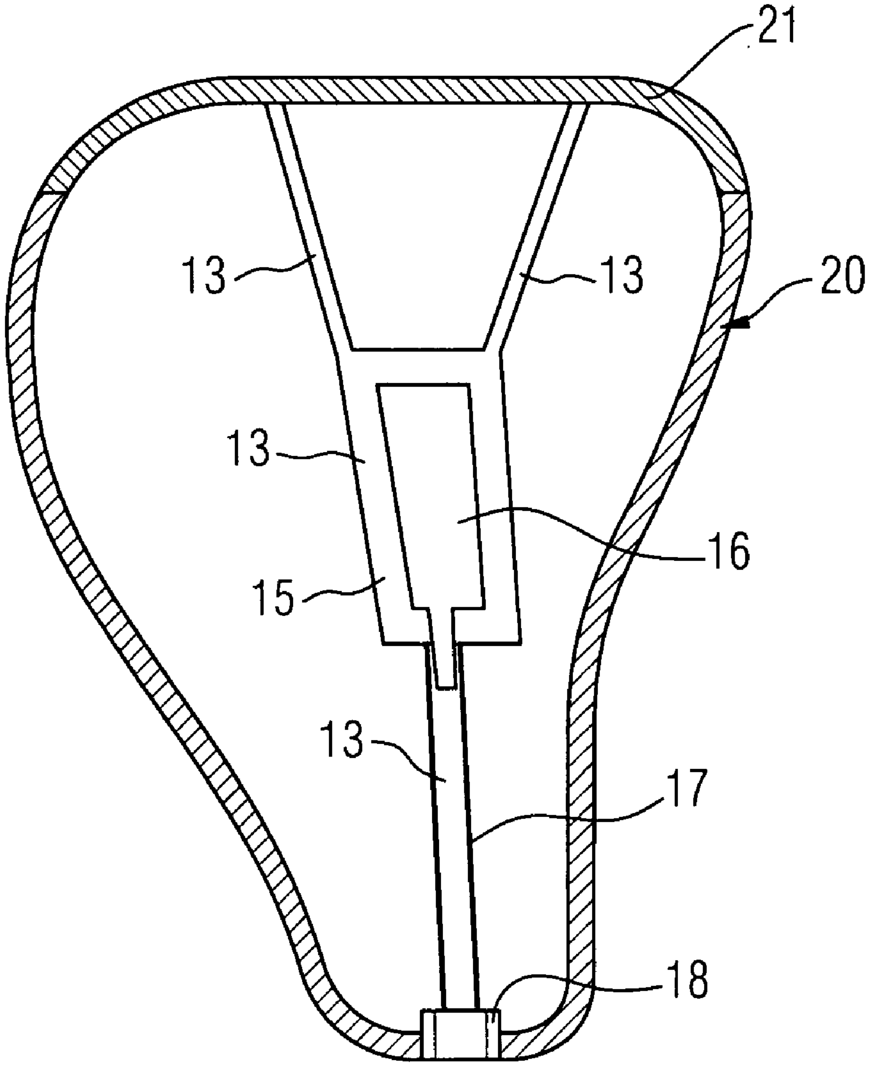

The third embodiment of the present invention illustrated in FIG. 3 largely corresponds to the second embodiment. The components in the inside of the hearing device such as the bands 13, the recess 15, the receiver 16, the receiver tube 17 and the sealing mechanism are identical to the components of the second exemplary embodiment. In this regard, reference is made to the above description of this component. According to the third embodiment, the hearing device housing is designed in two parts. It consists of a first housing part 20, which was referred to as a housing shell in conjunction with the second exemplary embodiment. A second housing part 21 seals the first housing part 20 completely. Accordingly, the rubber band 13 is affixed on the one hand to the housing part 20 and on the other hand to the second housing part 21. Naturally it remains possible to design the inner structure of the hearing device as depicted in the first exemplary embodiment for instance according to FIG. 1, so that the rubber band does not serve simultaneously as the receiver tube.

Advantages also emerge from this second and third embodiment, said advantages being illustrated in conjunction with the first embodiment.

The invention claimed is:

1. An in-the-ear hearing apparatus, comprising:

a first housing part;

a second housing part with which the first housing part can be sealed;

a flexible elastic element that is affixed on one hand to the first housing part and on another hand to the second housing part and pulls the second housing part onto the first housing part by a tension; and an electronic component attached to the elastic element, wherein the electronic component is selected from the group consisting of: a coil, a receiver, and a loudspeaker.

2. The in-the-ear hearing apparatus as claimed in claim 1, wherein the flexible elastic element can be extended in a longitudinal direction.

3. The in-the-ear hearing apparatus as claimed in claim 1, wherein the elastic element has a star shape and comprises at least three elastic ends.

4. The in-the-ear hearing apparatus as claimed in claim 3, wherein at least two of the three elastic ends are affixed to the second housing part.

5. The in-the-ear hearing apparatus as claimed in claim 1, wherein the electronic component is attached in a center of the elastic element.

6. The in-the-ear hearing apparatus as claimed in claim 1, wherein the elastic element comprises a band segment having a tube shape.

7. The in-the-ear hearing apparatus as claimed in claim 6, wherein the tube-shaped band segment directs an output sound from a loudspeaker of the hearing apparatus to the first housing part.

8. The in-the-ear hearing apparatus as claimed in claim 6, wherein the tube-shaped band segment is attached to the first housing part and at least partially retains the second housing part in place.

9. The in-the-ear hearing apparatus as claimed in claim 1, wherein the elastic element is attached to a segment of the first housing part that faces an ear drum of a user of the hearing apparatus when the hearing apparatus is worn by the user.

10. The in-the-ear hearing apparatus as claimed in claim 9, wherein the segment of the first housing part does not rest against an auditory canal of the user.

11. The in-the-ear hearing apparatus as claimed in claim 1, wherein the second housing part comprises a module and the elastic element is affixed to the module of the second housing part.

12. The in-the-ear hearing apparatus as claimed in claim 11, wherein the module is a removable segment.

13. The in-the-ear hearing apparatus as claimed in claim 1, wherein the elastic element is affixed to an inside of the first housing part.

14. A method for manufacturing an in-the-ear hearing apparatus, comprising:

arranging a first housing part and a second housing part of the hearing apparatus wherein the first housing part can be sealed by the second housing part;

affixing an elastic element on one end to the first housing part and on another end to the second housing part wherein the elastic element can be extended in a longitudinal direction;

sealing the first housing part by pulling the second housing part onto the first housing part with a tension of the elastic element; and attaching an electronic component to the elastic element, wherein the electronic component is selected from the group consisting of: a coil, a receiver, and a loudspeaker.

15. The method as claimed in claim 14, wherein the elastic element has a star shape and comprises at least three elastic ends.

16. The method as claimed in claim 14, wherein the elastic element comprises a band segment having a tube shape.

17. The method as claimed in claim 14, wherein the tube-shaped band segment directs an output sound from a loudspeaker of the hearing apparatus to the first housing part.

* * * * *